United States Patent
Pornsuriyasak

(10) Patent No.: US 10,584,090 B2
(45) Date of Patent: Mar. 10, 2020

(54) COMPOSITION AND A PROCESS FOR A PREPARATION OF POLYURETHANE DISPERSION

(71) Applicant: PTT Global Chemical Public Company Limited, Bangkok (TH)

(72) Inventor: Papapida Pornsuriyasak, Bangkok (TH)

(73) Assignee: PTT Global Chemical Public Company Limited (TH)

( * ) Notice: Subject to any disclaimer, the term of this patent is extended or adjusted under 35 U.S.C. 154(b) by 128 days.

(21) Appl. No.: 15/735,862

(22) PCT Filed: Jun. 16, 2016

(86) PCT No.: PCT/TH2016/000055
§ 371 (c)(1),
(2) Date: Dec. 12, 2017

(87) PCT Pub. No.: WO2016/204702
PCT Pub. Date: Dec. 22, 2016

(65) Prior Publication Data
US 2019/0202966 A1 Jul. 4, 2019

(30) Foreign Application Priority Data

Jun. 17, 2015 (TH) ................................. 1501003379

(51) Int. Cl.
| | |
|---|---|
| C07C 59/105 | (2006.01) |
| C08G 18/75 | (2006.01) |
| C09D 175/04 | (2006.01) |
| C09J 175/04 | (2006.01) |
| C08G 18/32 | (2006.01) |
| C08G 18/80 | (2006.01) |

(Continued)

(52) U.S. Cl.
CPC ............ C07C 59/105 (2013.01); C07C 69/73 (2013.01); C08G 18/0823 (2013.01); C08G 18/246 (2013.01); C08G 18/3206 (2013.01); C08G 18/3221 (2013.01); C08G 18/36 (2013.01); C08G 18/755 (2013.01); C08G 18/8051 (2013.01); C08K 5/053 (2013.01); C08K 5/29 (2013.01); C08K 5/3432 (2013.01); C08L 75/06 (2013.01); C09D 175/04 (2013.01); C09J 175/04 (2013.01); C08L 2201/54 (2013.01)

(58) Field of Classification Search
CPC .. C08G 18/36; C08G 18/246; C08G 18/3221; C08G 18/755; C08G 18/0823; C08G 18/8051; C08G 18/3206; C08L 75/06; C08L 2201/54; C08K 5/3432; C08K 5/053; C08K 5/29; C09D 175/04; C07C 59/105; C07C 69/73; C09J 175/04
See application file for complete search history.

(56) References Cited

U.S. PATENT DOCUMENTS

| 4,368,231 A | 1/1983 | Egert et al. |
| 5,512,655 A | 4/1996 | Klauck et al. |

(Continued)

FOREIGN PATENT DOCUMENTS

| CA | 2004723 C | 3/1997 |
| CA | 2001723 C | 7/2000 |

(Continued)

OTHER PUBLICATIONS

Jiang et al., "Blood compatibility of polyurethane surface grafted copolymerization with sulfobetaine monomer", Colloids and Surfaces B, vol. 36, pp. 27-33 (2004).

(Continued)

*Primary Examiner* — Rabon A Sergent
(74) *Attorney, Agent, or Firm* — Kim IP Law Group PLLC

(57) ABSTRACT

This invention relates to a composition for a preparation of polyurethane dispersion, comprising bio-based polyol as shown in structure (I) and polyhydroxy fatty acid compound as shown in structure (II): wherein, R represents a polyhydric alcohol unit that is selected from aliphatic polyhydric alcohol, alicyclic polyhydric alcohol, cyclic polyhydric alcohol, aromatic polyhydric alcohol, or optionally, cyclic polyhydroxyl having heteroatom; R\ represents a hydrocarbon unit obtained from a molecular chain of unsaturated fatty acid having 14-24 carbon atoms and having from 1-6 pairs of vicinal diol group per one molecular chain of such unsaturated fatty acid; n represents an integer from 2 to 8 of an ester group obtained from a reaction of polyhydric alcohol and unsaturated fatty acid; wherein said composition is prepared from a process comprising the steps of: i. mixing fatty acid comprising unsaturated fatty acid and polyhydric alcohol at a ratio of 1 mole equivalent or more of carboxylic group from unsaturated fatty acid per a hydroxy group from polyhydric alcohol; ii. adding organic acid and peroxide compound into the mixture from step i.; iii. adding nucleophilic substance into the mixture from step ii. under acidic condition.

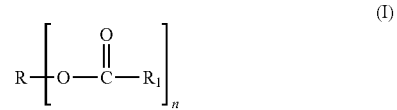

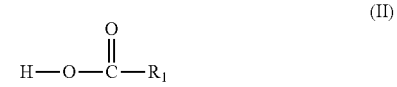

38 Claims, 1 Drawing Sheet

| (51) | Int. Cl. | |
|---|---|---|
| | *C08G 18/08* | (2006.01) |
| | *C07C 69/73* | (2006.01) |
| | *C08G 18/36* | (2006.01) |
| | *C08G 18/24* | (2006.01) |
| | *C08K 5/053* | (2006.01) |
| | *C08K 5/29* | (2006.01) |
| | *C08K 5/3432* | (2006.01) |
| | *C08L 75/06* | (2006.01) |

(56) References Cited

U.S. PATENT DOCUMENTS

| 7,629,478 B2 | 12/2009 | Soi et al. |
|---|---|---|
| 2012/0214938 A1 | 8/2012 | Mannari |

FOREIGN PATENT DOCUMENTS

| CN | 103232372 A | 8/2013 |
|---|---|---|
| EP | 0132941 A1 | 2/1985 |
| EP | 0132941 A1 | 5/1991 |
| WO | 2011112923 A2 | 9/2011 |

OTHER PUBLICATIONS

Zetterlund et al., Thermal and Mechanical Properties of Polyurethanes Derived from Mono- and Disaccharides, Polymer International, vol. 42, pp. 1-8 (1997).

Jiang et al., Blood compatibility of polyurethane surface grafted copolymerization with sulfobetaine monomer, Colloids and Surfaces B, vol. 36, pp. 27-33 (2003).

Yan et al., Thermoplastic Cellulose-graft-poly(L-lactide) Copolymers Homogeneously Synthesized in an Ionic Liquid with 4-Dimethylaminopyridine Catalyst, vol. 10, No. 8, pp. 2013-2018 (2009).

Written Opinion of the International Searching Authority dated May 26, 2017.

International Search Report for PCT/TH2016/0000555 dated May 26, 2017.

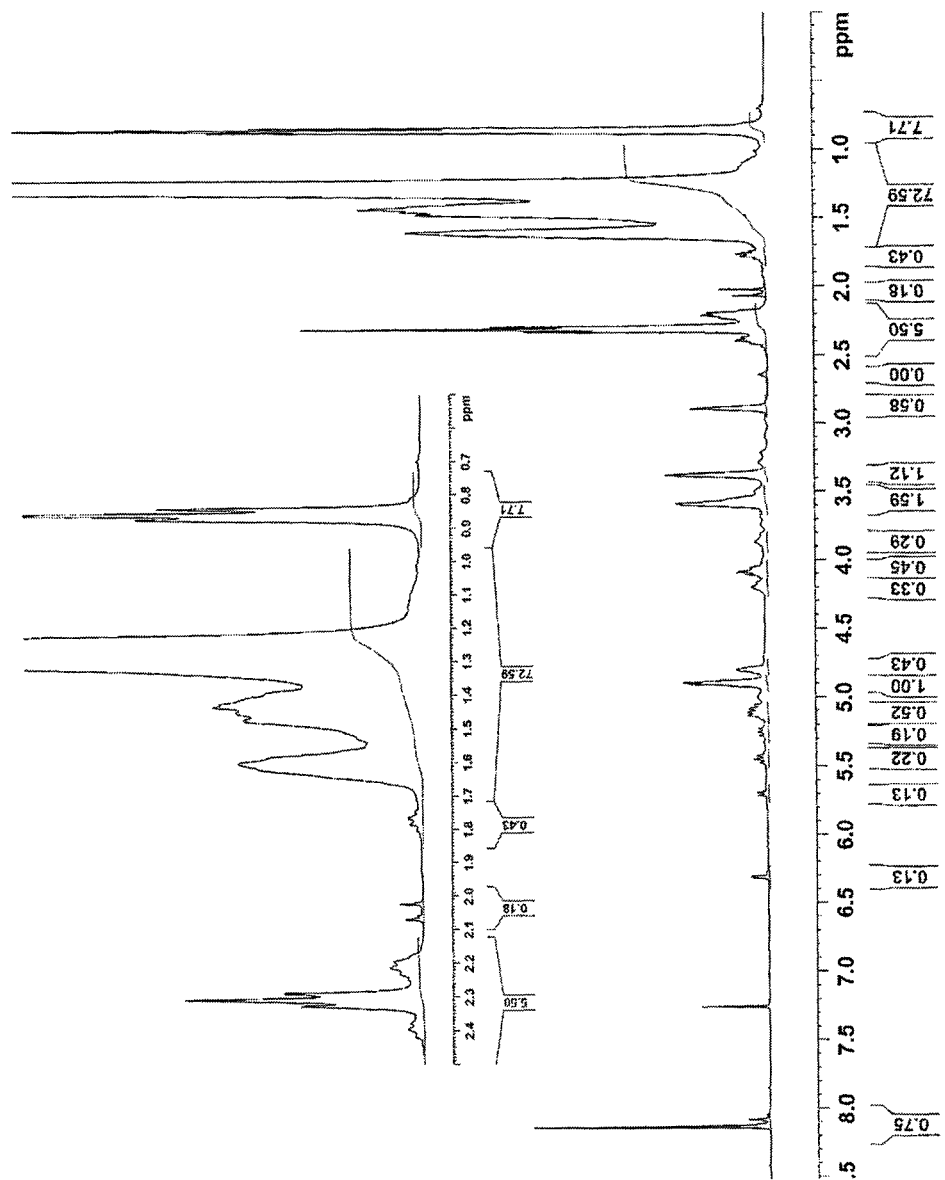

COMPOSITION AND A PROCESS FOR A PREPARATION OF POLYURETHANE DISPERSION

CROSS-REFERENCE TO RELATED APPLICATIONS

This application is a 371 national phase application of International Patent Application No. PCT/TH2016/000055, filed Jun. 16, 2016, which claims foreign priority to Thailand patent application no, 1501003379 filed Jun. 17, 2015, the entire disclosures of which are hereby, incorporated by reference herein in their entireties.

FIELD OF THE INVENTION

This invention is in a field of chemistry relating to the composition for the preparation of polyurethane dispersion and the process for preparing such composition.

BACKGROUND OF THE INVENTION

Polyurethane has been used widely in surface coating industry such as adhesive, ink, and colour coating. At present, water-based polyurethane dispersions (PUDs) are a rapidly growing segment of the polyurethane coating industry due to their versatility and environmentally friendly with zero to low volatile organic content (VOC). Moreover, the water-based polyurethane has low viscosity although the polymer chain itself has high molecular weight. This makes it available in a wide range of hardness and solid content for suitable formulation into a compliant coating on many different substrates. Polyurethane can be prepared from isocyanate and polyol compounds such as polyester polyol or polyether polyol, which can be prepared either from petroleum or bio-based source such as vegetable oil, starch, carbohydrate, or bio-based substances from fermentation process.

Polyester polyol can be prepared in many ways. One of interesting ways is the preparation from epoxidation of glyceride compound such as U.S. Pat. No. 7,629,478B2 disclosed a preparation process for polyester polyol for polyurethane production by epoxidizing monoglyceride, which obtained from reaction between unsaturated fatty acid or unsaturated triglyceride, with polyhydric alcohol. The resulting product was then reacted with polyhydric alcohol such as sucrose resulting in epoxide ring opening to obtain polyester polyol. The ratio of fatty acid or triglyceride to polyhydric alcohol was about 4 to 6 mole of polyhydric alcohol per mole of fatty acid or triglyceride. However, this patent document did not mention the relationship of polyester polyol and its suitable application. Different polyester polyol structure was suitable for the production of different types of polyurethane which could affect the properties of polyurethane.

Apart from monoglyceride, polyglyceride has been used for the preparation of polyester polyol. Polyglyceride can be prepared in many ways such as European patent publication no. EP0132941A1 disclosed the preparation method for polyglyceride with higher number of fatty acid chain by transesterification of polyol with fatty acid ester in the absence of solvent. Canadian patent publication no. CA2004723A1 mentioned polyglyceride obtained from transesterification of soil been oil and sugar with hydroxyl group. However, polyglyceride obtained from those patent documents were suitable to be used as emulsifier in food and medical applications because of low hydroxy group on their structures and its solid form at ambient temperature, which was not suitable for using in polyurethane production especially in coating applications. Therefore, the present invention focuses on polyester polyol composition from polyglyceride for the production of polyurethane dispersion which has not been disclosed so far.

In the preparation of polyurethane dispersion, normally internal emulsifier is added to provide ionic charge on polyurethane chain. The ionic charge, that a polymer molecule carries on it, needed to be controlled in an appropriate number to obtain polyurethane with high stability in aqueous media. However, it also depends on other parameters such as nature of polymer and neutralization rate between carboxylic acid and base functional groups. Internal emulsifier for the preparation of polyurethane dispersion such as dihydroxy fatty acid compound according to U.S. Pat. No. 5,512,655, or hydrophilic dihydroxy sulfonate monomer according to Chinese patent no. CN103232372, or 1,2-disubstituted oxyethylene according to patent publication no. US20120214938A1. Said internal emulsifiers need to be added into system during the preparation of polyurethane prepolymerization, which is complicated and need more steps in working process.

SUMMARY OF THE INVENTION

The present invention aims to develop a composition for a preparation of polyurethane dispersion that can be prepared by simple process and can be applied without an addition of internal emulsifier.

The invention relates to a composition for a preparation of polyurethane dispersion and a process for preparing such composition. The composition for the preparation of polyurethane dispersion comprises bio-based polyol as shown in structure (I) and polyhydroxy fatty acid compound as shown in structure (II):

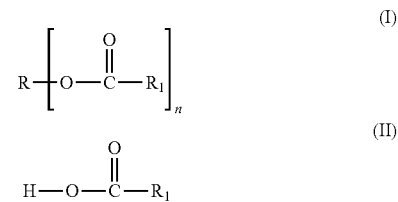

wherein,

R represents a polyhydric alcohol unit that is selected from aliphatic polyhydric alcohol, alicyclic polyhydric alcohol, cyclic polyhydric alcohol, aromatic polyhydric alcohol, or optionally, cyclic polyhydroxyl having heteroatom;

$R_1$ represents a hydrocarbon unit obtained from a molecular chain of unsaturated fatty acid having 14-24 carbon atoms and having from 1-6 pairs of vicinal diol group per one molecular chain of such unsaturated fatty acid;

n represents an integer from 2 to 8 of an ester group obtained from a reaction of polyhydric alcohol and unsaturated fatty acid;

wherein said composition is prepared from a process comprising the steps of:

i. mixing fatty acid comprising unsaturated fatty acid and polyhydric alcohol at a ratio of 1 mole equivalent or more of carboxylic group from unsaturated fatty acid per a hydroxy group from polyhydric alcohol;

ii. adding organic acid and peroxide compound into the mixture from step i.;

iii. adding nucleophilic substance into the mixture from step ii. under acidic condition.

BRIEF DESCRIPTION OF THE DRAWINGS

FIG. 1 shows proton-nuclear magnetic resonance spectrum of bio-based polyol of structure (I) measured at the frequency of 400 MHz by dissolving bio-based polyol of structure (I) in deuterated chloroform ($CDCl_3$). The chemical shift results are as the following: 0.86 (m, $CH_3$ of fatty chain), 1.27 (m, $CH_2$ of fatty chain), 1.43 (m, $CH_2$ of fatty acid), 1.61 (m, $CH_2$ of fatty acid), 2.32-2.45 (m, OH, CHOH), 2.89 (m), 3.36 (m), 3.55 (m), 3.86 (m), 4.08 (m), 4.20 (m), 4.76-4.82 (m), 4.85-4.90 (m), 4.95-5.15 (m), 5.24 (dd), 5.44 (dd), 5.70 (d, β H-1), 6.31 (d, α H-1) ppm.

DETAILED DESCRIPTION OF THE INVENTION

Definition

Technical terms or scientific terms used herein, unless stated otherwise, have their definitions as known in persons skilled in the art.

Any tool, equipment, method, or chemical mentioned herein shall mean tool, equipment, method, or chemical being used or practiced generally by a person skilled in the art of this field unless stated otherwise that they are tools, equipment, methods, or chemicals specific only in this invention.

Use of singular nouns or pronouns when used with "comprising" in claims and/or specification means "one" and will also include "one or more", "at least one", and "one or more than one".

Throughout this application, the term "about" used to indicate any value that is appeared or expressed herein may be varied or deviated, which the variation or deviation may occur from the error of instruments and methods used to determine various values.

"Heteroatom" means non-carbon atoms, including but not limited to, tetrels, for example, silicon, germanium, tin and lead; pniktogens, for example, nitrogen, phosphorus, arsenic, antimony and bismuth; chalcogens, for example, oxygen, sulfur, selenium, and tellurium; halogens, for example, fluorine, chlorine, bromine and iodine.

"Polyhydroxy fatty acid compound" means fatty acid compound with at least 2 hydroxy groups.

The objective of this invention is the composition for the preparation of polyurethane dispersion comprising bio-based polyol and hydroxy fatty acid as internal emulsifier in the system.

Another objective is the preparation process for composition comprising bio-based polyol and polyhydroxy fatty acid compound for the preparation of polyurethane dispersion.

The composition according to this invention provides positive charge to the obtained polyurethane, giving good ionic interaction to the material with negative charge on the surface such as wool or glass. Therefore, it is suitable for using as adhesive and coagulant. Moreover, more hydroxy groups on bio-based polyol molecule will promote crosslinking during polymerization, resulting in polyurethane with high strength, chemical and heat resistance comparing to the polyurethane synthesized from natural oil. In addition, said polyol obtained from monosaccharide and fatty acid can be classified into bio-based product.

The following details describe the preferred embodiments of the invention, and are not intended to limit the scope of the invention in any way.

The composition for the preparation of polyurethane dispersion, comprising bio-based polyol as shown in structure (I) and polyhydroxy fatty acid compound as shown in structure (II):

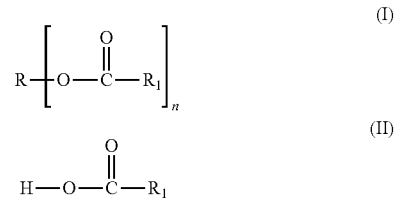

wherein,

R represents a polyhydric alcohol unit that is selected from aliphatic polyhydric alcohol, alicyclic polyhydric alcohol, cyclic polyhydric alcohol, aromatic polyhydric alcohol, or optionally, cyclic polyhydroxyl having heteroatom;

$R_1$ represents a hydrocarbon unit obtained from a molecular chain of unsaturated fatty acid having 14-24 carbon atoms and having from 1-6 pairs of vicinal diol group per one molecular chain of such unsaturated fatty acid;

n represents an integer from 2 to 8 of an ester group obtained from a reaction of polyhydric alcohol and unsaturated fatty acid;

wherein said composition is prepared from a process comprising the steps of:

i. mixing fatty acid comprising unsaturated fatty acid and polyhydric alcohol at a ratio of 1 mole equivalent or more of carboxylic group from unsaturated fatty acid per a hydroxy group from polyhydric alcohol;

ii. adding organic acid and peroxide compound into the mixture from step i.;

iii. adding nucleophilic substance into the mixture from step ii. under acidic condition.

In one embodiment, $R_1$ is unsaturated fatty acid that may be selected from oleic acid, myristoleic acid, palmitoleic acid, gadoleic acid, erucic acid, nervonic acid, linoleic acid, arachidonic acid, linoleic acid, linoelaidic acid, docosahexaenoic acid, eicosapentaenoic acid, elaidic acid, sapienic acid, vaccenic acid, or a mixture thereof. Preferably, unsaturated fatty acid is oleic acid.

In one embodiment, aliphatic polyhydric alcohol may be selected from ethylene glycol, glycerine, pentaerythritol, diethylene glycol, triethylene glycol, erythritol, threitol, propanediol-1,2-butylene, or a mixture thereof.

In one embodiment, alicyclic polyhydric alcohol may be selected from arabitol, sorbitol, xylitol, ribitol, adonitol, mannitol, dulcitol, galactitol, fucitol, iditol, inositol, volemitol, isomalt, maltitol, lactitol, maltotriitol, or a mixture thereof.

In one embodiment, cyclic polyhydric alcohol may be selected from glucose, galactose, mannose, dextrose, fucose, arabinose, altrose, gulose, hammelose, lyxose, ribose, thalose, xylose, allose, lactose, sucrose, maltose, isomaltotriose, maltotriose, raffinose, kestose, or a mixture thereof. Preferably, cyclic polyhydric alcohol is glucose.

In one embodiment, aromatic polyhydric alcohol may be selected from bis(4-hydroxyphenyl)(cyclo)alkane selected from 2,2-bis(4-hydroxyphenyl)propane, bis(4-hydroxyphenyl)methane, bis(4-hydroxyphenyl)ethane, or 1,1-bis(4-hydroxyphenyl)cyclohexane.

In one embodiment, the process according to step i. comprises an esterifying agent selected from carbodiimide compound. Preferably, the carbodiimide compound is dicyclohexylcarbodiimide. More preferably, the process according to step i. comprises esterifying agent and 4-dimethylaminopyridine to accelerate the reaction.

In one embodiment, the process according to step i. is performed at a room temperature with reaction time of at least 6 hours. In the process according to step iii., the nucleophilic substance is water and the process is performed at the temperature of 100-180° C. with reaction time of at least 2 hours.

In a preferred embodiment, the composition for the preparation of polyurethane dispersion according to the invention comprises polyhydroxy fatty acid compound in an amount of 4 to 16% by weight.

In another preferred embodiment, the composition for the preparation of polyurethane dispersion according to the invention has OH number of at least 120.

Another objective of this invention is to disclose the process for preparing the composition for the preparation of polyurethane dispersion comprising bio-based polyol as shown in structure (I) and polyhydroxy fatty acid compound as shown in structure (II), comprising the steps of:

i. mixing fatty acid comprising unsaturated fatty acid and polyhydric alcohol at a ratio of 1 mole equivalent or more of carboxylic group from unsaturated fatty acid per a hydroxy group from polyhydric alcohol;

ii. adding organic acid and peroxide compound into the mixture from step i.;

iii. adding nucleophilic substance into the mixture from step ii. under acidic condition.

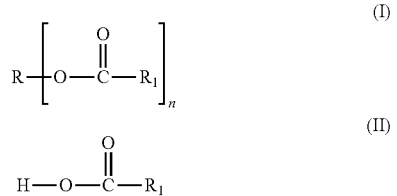

wherein,

R represents a polyhydric alcohol unit that is selected from aliphatic polyhydric alcohol, alicyclic polyhydric alcohol, cyclic polyhydric alcohol, aromatic polyhydric alcohol, or optionally, cyclic polyhydroxyl having heteroatom;

$R_1$ represents a hydrocarbon unit obtained from a molecular chain of unsaturated fatty acid having 14-24 carbon atoms and having from 1-6 pairs of vicinal diol group per one molecular chain of such unsaturated fatty acid;

n represents an integer from 2 to 8 of an ester group obtained from a reaction of polyhydric alcohol and unsaturated fatty acid.

In one embodiment, $R_1$ is unsaturated fatty acid selected from oleic acid, myristoleic acid, palmitoleic acid, gadoleic acid, erucic acid, nervonic acid, linolenic acid, arachidonic acid, linoleic acid, linoelaidic acid, docosahexaenoic acid, eicosapentaenoic acid, elaidic acid, sapienic acid, vaccenic acid, or a mixture thereof, preferably is oleic acid.

In one embodiment, aliphatic polyhydric alcohol may be selected from ethylene glycol, glycerine, pentaerythritol, diethylene glycol, triethylene glycol, erythritol, threitol, propanediol-1,2-butylene, or a mixture thereof.

In one embodiment, alicyclic polyhydric alcohol may be selected from arabitol, sorbitol, xylitol, ribitol, adonitol, mannitol, dulcitol, galactitol, fucitol, iditol, inositol, volemitol, isomalt, maltitol, lactitol, and maltotriitol, or mixture thereof.

In one embodiment, cyclic polyhydric alcohol may be selected from glucose, galactose, mannose, dextrose, fucose, arabinose, altrose, gulose, hammelose, lyxose, ribose, thalose, xylose, allose, lactose, sucrose, maltose, isomaltotriose, maltotriose, raffinose, kestose, or a mixture thereof, preferably is glucose.

In one embodiment, aromatic polyhydric alcohol is bis (4-hydroxyphenyl)(cyclo)alkane.

In one embodiment, the process according to step i. comprises an esterifying agent which is carbodiimide compound. Preferably, the carbodiimide compound is dicyclohexylcarbodiimide, wherein the process according to step i. comprises the esterifying agent and 4-dimethylaminopyridine to accelerate the reaction.

In one embodiment, the process according to step i. is performed at a room temperature with reaction time of at least 6 hours. In the process according to step iii., the nucleophilic substance is water and the process is performed at the temperature of 100-180° C. with reaction time of at least 2 hours.

In a preferred embodiment, the composition for the preparation of polyurethane dispersion according to the invention comprises polyhydroxy fatty acid compound in an amount of 4 to 16% by weight.

In another preferred embodiment, the composition for the preparation of polyurethane dispersion according to the invention has OH number of at least 120.

The following is the example of the preparation of the composition for a preparation of polyurethane dispersion according to this invention without any purpose to limit the scope of the invention in anyway.

Preparation of Polyglyceride 8.0 g of glucose, 62.8 to 81.6 g of oleic acid (calculated as mole equivalent ratio of hydroxyl group from polyhydric alcohol to carboxylic group from fatty acid about 1:5.0 to 1:6.5) were dissolved in 200 mL of dichloromethane under inert atmosphere. 18.3 g of dicyclohexylcarbodiimide and 1.1 g of 4-dimethylaminopyridine were mixed in 200 mL of dichloromethane. Then, the obtained solution was slowly added into glucose and oleic acid solution within 30 min, stirred at room temperature for 30 min. The mixture was stirred at room temperature for 18 hours under inert atmosphere. When reaction was completed, the resulting mixture was filtered to remove white precipitate out, then the filtrate was evaporated to obtain yellow syrup which was the mixture of polyglyceride and free fatty acid with percentage of product yield and percentage of fatty acid residue from the reaction as shown in table 1.

Comparative Example A 200 mg of glucose and 0.15 mL of triethylamine were dissolved in 10 mL of dichloromethane under inert atmosphere. Then, 2.16 mL of chloro-oleate was slowly added into the solution of glucose and triethylamine. The reaction mixture was stirred at room temperature for 16 hours. When reaction was completed, the resulted mixture was evaporated to obtain yellow slurry which was polyglyceride with percentage of product yield and percentage of fatty acid residue from the reaction as shown in table 1.

Comparative Example B 1.0 g of glucose and 9.4 g of oleic acid were dissolved in 20 mL of toluene under inert atmosphere. Then, 34.3 g of boric acid was slowly added into the solution of glucose and oleic acid. The mixture was stirred at 110° C. for 8 hours. Distillation equipment was assembled comprising condenser and Dean-Stark to remove water generated during the reaction. When reaction was completed, the resulted mixture was evaporated to obtain yellow slurry which was polyglyceride with percentage of product yield and percentage of fatty acid residue from the reaction as shown in table 1.

Preparation of Bio-Based Polyol and Polyhydroxy Fatty Acid Compound 26 mL of 95% formic acid was slowly added into 66 g of polyglyceride. Then, reaction temperature was reduced to 0° C., and 47 mL of 30% hydrogen peroxide was added dropwise in a duration of 45 min. The reaction mixture was stirred at the temperature of 0° C. and gradually increased to room temperature for 18 hours. Upon completion, the reaction mixture was diluted with 300 mL of dichloromethane and washed with 200 mL of water several times until neutral. The organic layer was evaporated under reduced pressure to obtain epoxidized polyglyceride.

70 g of epoxidized polyglyceride was diluted with 50 mL of water. Then, 14 mL of 95% acetic acid was added. The mixture was refluxed at the temperature of 110° C. for 4 hours. When reaction was completed, the obtained mixture was diluted with 300 mL of dichloromethane and washed with 200 mL of water several times until neutral. The organic layer was evaporated under reduced pressure to obtain a mixture of bio-based polyol and polyhydroxy fatty acid compound. The OH number of corresponding polyol mixture was analyzed as shown in table 1.

TABLE 1

Effect of the amount of oleic acid to polyglyceride yield and fatty acid residue from the reaction and OH number of the composition obtained from the mixture of polyglyceride and fatty acid in different ratios

| Example | Amount of oleic acid (g) | Percentage of polyglyceride yield compared with starting polyhydric alcohol | Percentage of fatty acid residue compared with starting mixture | OH number of the composition according to this invention |
|---|---|---|---|---|
| A | oleate/triethylamine | 51 | 0 | 79 |
| B | oleic/boric acid | 26 | 55 | 184 |
| 1 | 62.8 | 74 | 3.9 | 177 |
| 2 | 65.3 | 90 | 6.1 | 185 |
| 3 | 69.0 | 95 | 13.4 | 229 |
| 4 | 72.8 | 92 | 16.8 | 266 |
| 5 | 75.3 | 98 | 19 | 280 |
| 6 | 81.6 | 95 | 25 | 315 |

Preparation of Polyurethane Dispersion

One objective of the invention is the preparation of polyurethane dispersion for the coating of adhesive and binding.

Polyurethane was prepared in 250 mL glass reactor equipped with high speed mechanical stirrer, nitrogen gas system, and condenser, wherein the preparation of polyurethane dispersion according to this invention may be performed by the following step:

dissolving 10 g of composition for the preparation of polyurethane dispersion in 10 mL of tetrahydrofuran;

slowly dropping 0.8-1.0 mL of triethylamine by controlling reaction temperature at around 60° C. for 1 hour to allow triethylamine to react with carboxylic acid moiety from polyhydroxy fatty acid compound;

dropping 0.2 mL of 700 ppm dibutyltin dilaurate catalyst and 2 mL of isophorone diisocyanate (IPDI) at the rate of 1 mL/min, stirring the mixture at the speed of 200 rpm for about 3 hours under nitrogen atmosphere;

dropping 1,4-butanediol as molecular weight enhancing agent of polyurethane and for quenching isocyanate residue leftover from the reaction;

after polymerization reaction was completed, reducing reaction temperature to 30° C. and dropping 10 mL of water at the rate of 0.5 mL/min and stirring at the rate of 400-800 rpm, then continue stirring for 1 hour;

after completing the dispersion of polyurethane in water, evaporating organic solvent using rotary evaporator at the temperature about 30° C. to obtain high stability water based polyurethane dispersion.

After being left for 4 weeks, it was found that polyurethane prepared from example 1 to 4 still well dispersed in water, whereas polyurethane prepared from example 5 and 6 did not disperse in water.

TABLE 2

Molecular weight and average particle size of polyurethane dispersion obtained from example A, B, and 1 to 6

| Example | Molecular weight of polyurethane | Average particle size (nm) |
|---|---|---|
| A | 16556 | N/A |
| B | 19952 | N/A |
| 1 | 36205 | 530 |
| 2 | 39040 | 320 |
| 3 | 33166 | 110 |
| 4 | 28293 | 90 |
| 5 | 29088 | 150 |
| 6 | 30112 | 170 |

Note:

N/A means particle size could not be measured because polyurethane did not disperse in water.

TABLE 3

Effect of mixing speed in the preparation of polyurethane dispersion prepared from example 2

| Mixing speed (rpm) | Molecular weight of polyurethane | Average particle size (micron) |
|---|---|---|
| 400 | 39040 | 900 |
| 500 | 32450 | 870 |
| 600 | 35994 | 801 |
| 700 | 29512 | 512 |
| 800 | 30905 | 375 |

BEST MODE OF THE INVENTION

Best mode or preferred embodiment of the invention is as provided in the description of the invention.

The invention claimed is:

1. A composition for a preparation of polyurethane dispersion, comprising a bio-based polyol as shown in structure (I) and a polyhydroxy fatty acid compound as shown in structure (II):

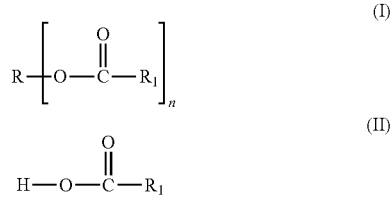

wherein,
R represents a polyhydric alcohol unit that is selected from aliphatic polyhydric alcohols, alicyclic polyhydric alcohols, cyclic polyhydric alcohols, aromatic polyhydric alcohols, and polyhydric cyclic units comprising a heteroatom;
$R_1$ represents a hydrocarbon unit obtained from a molecular chain of an unsaturated fatty acid having 14-24 carbon atoms, said hydrocarbon unit having 1-6 vicinal diol substituent(s);
n represents an integer from 2 to 8 of an ester group obtained from a reaction of a polyhydric alcohol and an unsaturated fatty acid;
wherein said composition is prepared from a process comprising the steps of:
(i) mixing a fatty acid comprising unsaturated fatty acid and a polyhydric alcohol at a ratio of more than 1 mole equivalent of carboxylic group from the unsaturated fatty acid per a hydroxy group from the polyhydric alcohol;
(ii) adding an organic acid and a peroxide compound into the mixture from step (i);
(iii) adding a nucleophilic substance into the mixture from step (ii) under acidic conditions.

2. The composition according to claim 1, wherein the unsaturated fatty acid is selected from oleic acid, myristoleic acid, palmitoleic acid, gadoleic acid, erucic acid, nervonic acid, linolenic acid, arachidonic acid, linoleic acid, linoelaidic acid, docosahexaenoic acid, eicosapentaenoic acid, elaidic acid, sapienic acid, vaccenic acid, or a mixture thereof.

3. The composition according to claim 2, wherein the unsaturated fatty acid is oleic acid.

4. The composition according to claim 1, wherein the aliphatic polyhydric alcohol is selected from arabitol, sorbitol, xylitol, ribitol, adonitol, mannitol, dulcitol, galactitol, fucitol, iditol, volemitol, ethylene glycol, glycerine, pentaerythritol, diethylene glycol, triethylene glycol, erythritol, threitol, propanediol-1,2-butylene, or a mixture thereof.

5. The composition according to claim 1, wherein the alicyclic polyhydric alcohol is selected from inositol, isomalt, maltitol, lactitol, maltotriitol, or a mixture thereof.

6. The composition according to claim 1, wherein the cyclic polyhydric alcohol is selected from glucose, galactose, mannose, dextrose, fucose, arabinose, altrose, gulose, hammelose, lyxose, ribose, thalose, xylose, allose, lactose, sucrose, maltose, isomaltotriose, maltotriose, raffinose, kestose, or a mixture thereof.

7. The composition according to claim 6, wherein the cyclic polyhydric alcohol is glucose.

8. The composition according to claim 1, wherein the aromatic polyhydric alcohol is bis(4-hydroxyphenyl)(cyclo)alkane.

9. The composition according to claim 1, wherein the process according to step (i) comprises an esterifying agent.

10. The composition according to claim 9, wherein the esterifying agent is carbodiimide compound.

11. The composition according to claim 10, wherein the carbodiimide compound is dicyclohexylcarbodiimide.

12. The composition according to claim 9, wherein the process according to step (i) comprises the esterifying agent and 4-dimethylaminopyridine.

13. The composition according to claim 1, wherein the process according to step (i) is performed at room temperature.

14. The composition according to claim 1, wherein said fatty acid comprising unsaturated fatty acid is mixed with said polyhydric alcohol in step (i) for at least 6 hours.

15. The composition according to claim 1, wherein the nucleophilic substance is water.

16. The composition according to claim 1, wherein the process according to step (iii) is performed at a temperature of 100-180° C.

17. The composition according to claim 1, wherein said nucleophilic substance is added in step (iii) and maintained into the mixture from step (ii) under acidic conditions for at least 2 hours.

18. The composition according to claim 1, wherein said composition comprises the polyhydroxy fatty acid compound of structure (II) in an amount of 4 to 16% by weight, based on the total weight of structures (I) and (II).

19. The composition according to claim 1, wherein said composition has an OH number of at least 120.

20. A process for preparing a composition for a preparation of polyurethane dispersion comprising a bio-based polyol as shown in structure (I) and a polyhydroxy fatty acid compound as shown in structure (II), comprising the steps of:
(i) mixing a fatty acid comprising unsaturated fatty acid and a polyhydric alcohol at a ratio of more than 1 mole equivalent of carboxylic group from the unsaturated fatty acid per a hydroxy group from the polyhydric alcohol;
(ii) adding an organic acid and a peroxide compound into the mixture from step (i);
(iii) adding a nucleophilic substance into the mixture from step (ii) under acidic conditions

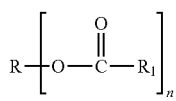
(I)

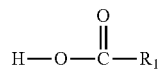
(II)

wherein,
R represents a polyhydric alcohol unit that is selected from aliphatic polyhydric alcohols, alicyclic polyhydric alcohols, cyclic polyhydric alcohols, aromatic polyhydric alcohols, and polyhydric cyclic units comprising a heteroatom;
$R_1$ represents a hydrocarbon unit obtained from a molecular chain of an unsaturated fatty acid having 14-24 carbon atoms, said hydrocarbon unit having 1-6 vicinal diol substituent(s);
n represents an integer from 2 to 8 of an ester group obtained from a reaction of a polyhydric alcohol and an unsaturated fatty acid.

21. The process for preparing the composition according to claim 20, wherein the unsaturated fatty acid is selected from oleic acid, myristoleic acid, palmitoleic acid, gadoleic acid, erucic acid, nervonic acid, linolenic acid, arachidonic acid, linoleic acid, linoelaidic acid, docosahexaenoic acid, eicosapentaenoic acid, elaidic acid, sapienic acid, vaccenic acid, or a mixture thereof.

22. The process for preparing the composition according to claim 21, wherein the unsaturated fatty acid is oleic acid.

23. The process for preparing the composition according to claim 20, wherein the aliphatic polyhydric alcohol is selected from arabitol, sorbitol, xylitol, ribitol, adonitol, mannitol, dulcitol, galactitol, fucitol, iditol, volemitol, ethylene glycol, glycerine, pentaerythritol, diethylene glycol, triethylene glycol, erythritol, threitol, propanediol-1,2-butylene, or a mixture thereof.

24. The process for preparing the composition according to claim 20, wherein the alicyclic polyhydric alcohol is selected from inositol, isomalt, maltitol, lactitol, maltotriitol, or a mixture thereof.

25. The process for preparing the composition according to claim 20, wherein the cyclic polyhydric alcohol is selected from glucose, galactose, mannose, dextrose, fucose, arabinose, altrose, gulose, hammelose, lyxose, ribose, thalose, xylose, allose, lactose, sucrose, maltose, isomaltotriose, maltotriose, raffinose, kestose, or a mixture thereof.

26. The process for preparing the composition according to claim 25, wherein the cyclic polyhydric alcohol is glucose.

27. The process for preparing the composition according to claim 20, wherein the aromatic polyhydric alcohol is bis(4-hydroxyphenyl)(cyclo)alkane.

28. The process for preparing the composition according to claim 20, wherein the process according to step (i) comprises an esterifying agent.

29. The process for preparing the composition according to claim 28, wherein the esterifying agent is a carbodiimide compound.

30. The process for preparing the composition according to claim 29, wherein the carbodiimide compound is dicyclohexylcarbodiimide.

31. The process for preparing the composition according to claim 28, wherein the process according to step (i) comprises the esterifying agent and 4-dimethylaminopyridine.

32. The process for preparing the composition according to claim 20, wherein the process according to step (i) is performed at room temperature.

33. The process for preparing the composition according to claim 20, wherein said fatty acid comprising unsaturated fatty acid is mixed with said polyhydric alcohol in step (i) for at least 6 hours.

34. The process for preparing the composition according to claim 20, wherein the nucleophilic substance is water.

35. The process for preparing the composition according to claim 20, wherein the process according to step (iii) is performed at a temperature of 100-180° C.

36. The process for preparing the composition according to claim 20, wherein the nucleophilic substance is added in step (iii) and maintained in the mixture from step (ii) under acidic conditions for at least 2 hours.

37. The process for preparing the composition according to claim 20, wherein the composition obtained from said process comprises the polyhydroxy fatty acid compound of structure (II) in an amount of 4 to 16% by weight, based on the total weight of structures (I) and (II).

38. The process for preparing the composition according to claim 20, wherein the composition obtained from said process has an OH number of at least 120.

* * * * *